United States Patent
Atkin et al.

(10) Patent No.: US 7,217,128 B2
(45) Date of Patent: May 15, 2007

(54) ULTRASONIC DENTAL INSERT HAVING INTERCHANGEABLE PLASTIC AND METAL TIPS

(75) Inventors: Benjamin Atkin, Miami, FL (US); Haim Levy, Hod Hasharon (IL)

(73) Assignee: Discus Dental Impressions, Inc., Culver City, CA (US)

( * ) Notice: Subject to any disclaimer, the term of this patent is extended or adjusted under 35 U.S.C. 154(b) by 0 days.

(21) Appl. No.: 10/735,147

(22) Filed: Dec. 12, 2003

(65) Prior Publication Data

US 2004/0126738 A1    Jul. 1, 2004

Related U.S. Application Data

(60) Provisional application No. 60/432,652, filed on Dec. 12, 2002.

(51) Int. Cl.
    *A61C 1/07* (2006.01)
(52) U.S. Cl. .................................................... 433/119
(58) Field of Classification Search ................ 433/118, 433/119, 165, 84, 82; 606/169, 170, 171
    See application file for complete search history.

(56) References Cited

U.S. PATENT DOCUMENTS

| | | | |
|---|---|---|---|
| 3,518,766 A * | 7/1970 | Emanuel ...................... 433/86 |
| 3,526,036 A * | 9/1970 | Goof .......................... 433/119 |
| 3,526,219 A | 9/1970 | Balamuth |
| 3,547,110 A | 12/1970 | Balamuth |
| 3,636,947 A | 1/1972 | Balamuth |
| 3,645,255 A | 2/1972 | Robinson |
| 3,651,576 A | 3/1972 | Massa |
| 3,654,502 A | 4/1972 | Carmona et al. |
| 3,809,977 A | 5/1974 | Balamuth et al. |
| 3,924,335 A | 12/1975 | Balamuth et al. |
| RE28,752 E | 3/1976 | Balamuth et al. |
| 4,169,984 A * | 10/1979 | Parisi ..................... 310/323.18 |
| 4,176,454 A | 12/1979 | Hatter et al. |
| 4,236,889 A | 12/1980 | Wright |
| RE30,536 E | 3/1981 | Perdreaux, Jr. |
| 4,260,380 A * | 4/1981 | Nash .......................... 433/119 |
| 4,331,422 A | 5/1982 | Heyman |
| 4,370,131 A | 1/1983 | Banko |
| 4,484,893 A * | 11/1984 | Finn .......................... 433/118 |
| 4,589,847 A * | 5/1986 | Loge et al. ................. 433/126 |
| 4,735,200 A | 4/1988 | Westerman |
| 4,787,847 A | 11/1988 | Martin et al. |
| 4,832,683 A | 5/1989 | Idemoto et al. |
| 5,039,304 A | 8/1991 | Heil |
| 5,286,192 A | 2/1994 | Dixon |
| 5,395,240 A | 3/1995 | Paschke et al. |
| 5,501,596 A | 3/1996 | Bailey |
| 5,531,597 A | 7/1996 | Foulkes et al. |

(Continued)

*Primary Examiner*—Cary E. O'Connor
(74) *Attorney, Agent, or Firm*—Christie, Parker & Hale, LLP

(57) ABSTRACT

An ultrasonic dental insert for an ultrasonic dental tool is provided. The ultrasonic dental insert includes a transducer, a connecting body, a hand grip, at least one O-ring and a removable tip. The transducer generates ultrasonic vibrations. The connecting body has a proximal end attached to the transducer and a distal end. The distal end has an engagement portion formed thereon. The hand grip envelopes at least a portion of the connecting body. At least one O-ring is for shock absorption, and is mounted between the connecting body and the hand grip and around the engagement portion. The removable tip engages the engagement portion.

25 Claims, 5 Drawing Sheets

U.S. PATENT DOCUMENTS

| | | |
|---|---|---|
| 5,655,906 A | 8/1997 | Coss et al. |
| 5,704,787 A | 1/1998 | Hickok et al. |
| 5,772,434 A | 6/1998 | Winston |
| 5,775,901 A | 7/1998 | Riso |
| 5,853,290 A * | 12/1998 | Winston ............... 433/86 |
| 6,012,922 A | 1/2000 | Novak |
| 6,086,369 A * | 7/2000 | Sharp et al. ............ 433/118 |
| 6,386,866 B1 | 5/2002 | Hecht et al. |
| 2002/0040198 A1 | 4/2002 | Rahman et al. |
| 2002/0127512 A1 | 9/2002 | Chen et al. |
| 2003/0022129 A1 | 1/2003 | Rahman et al. |
| 2003/0073055 A1 | 4/2003 | Pollock et al. |
| 2003/0108844 A1 | 6/2003 | Rahman et al. |

* cited by examiner

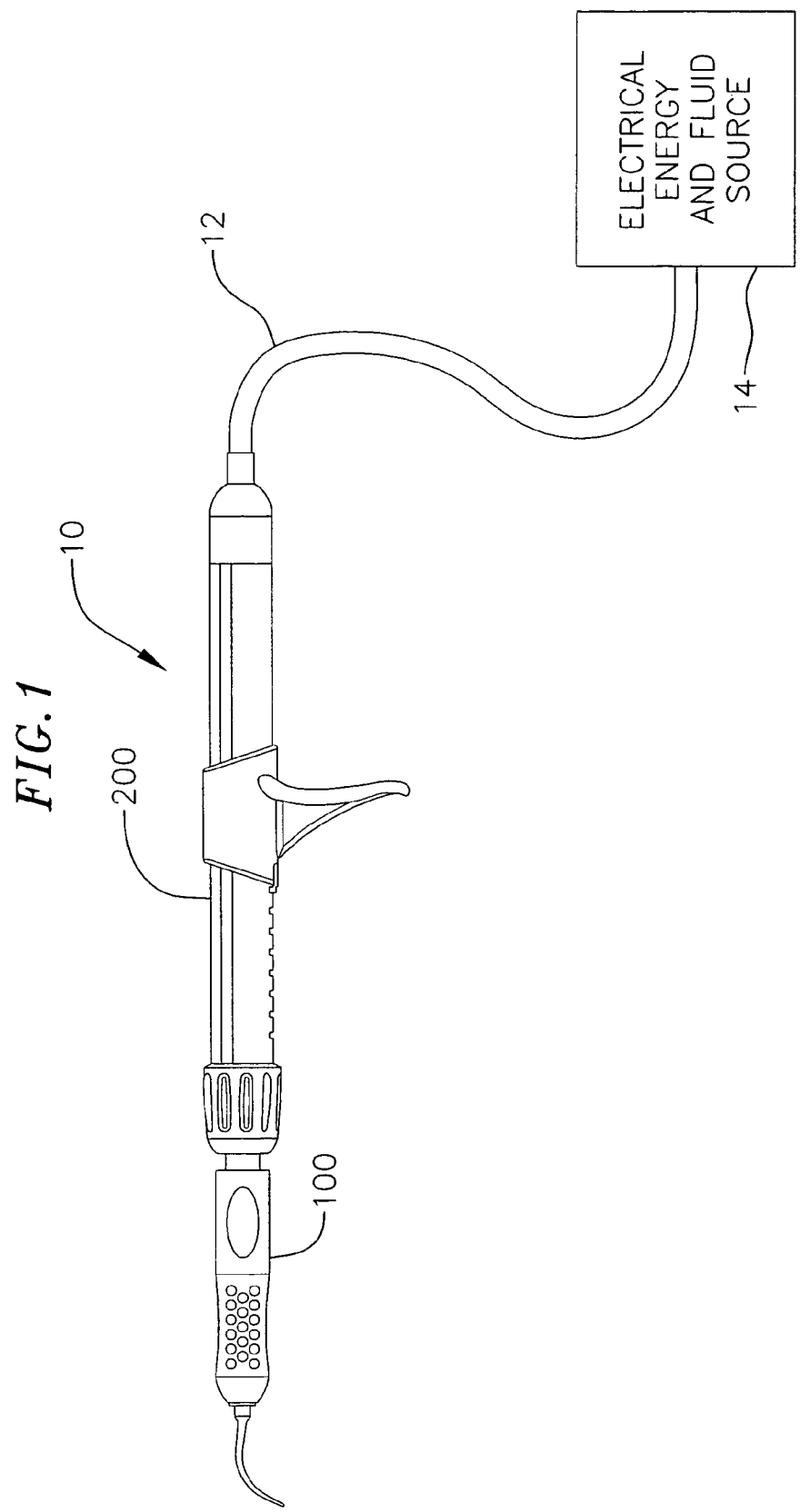

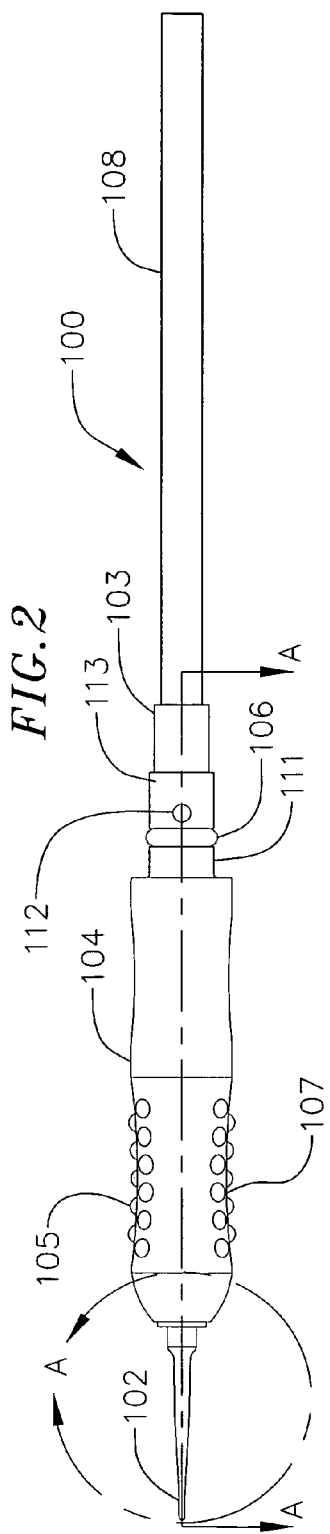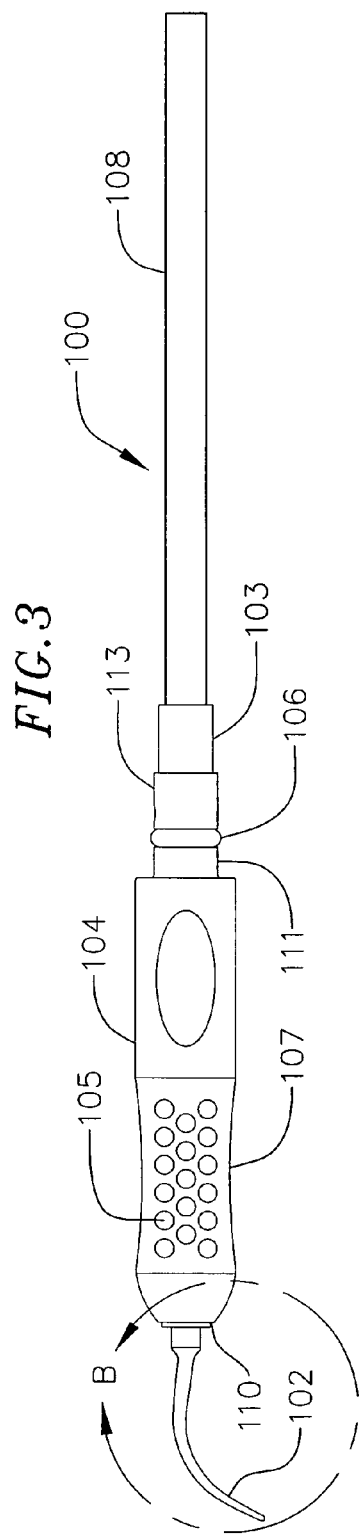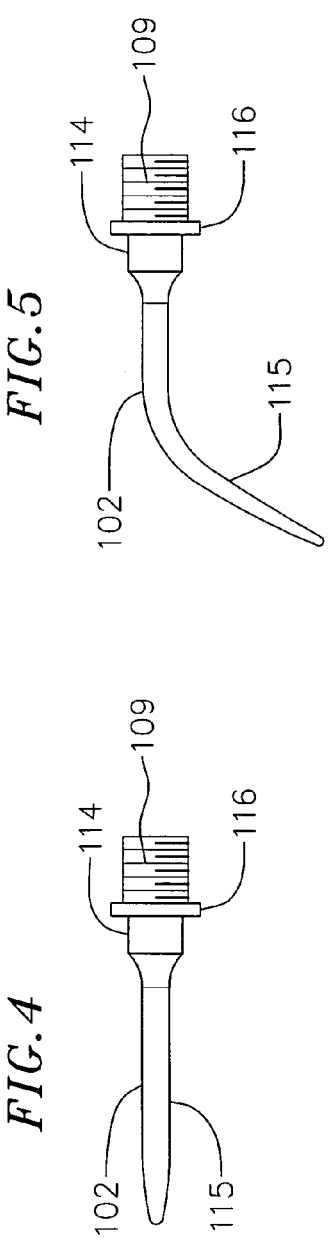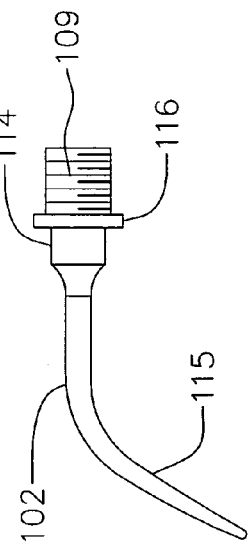

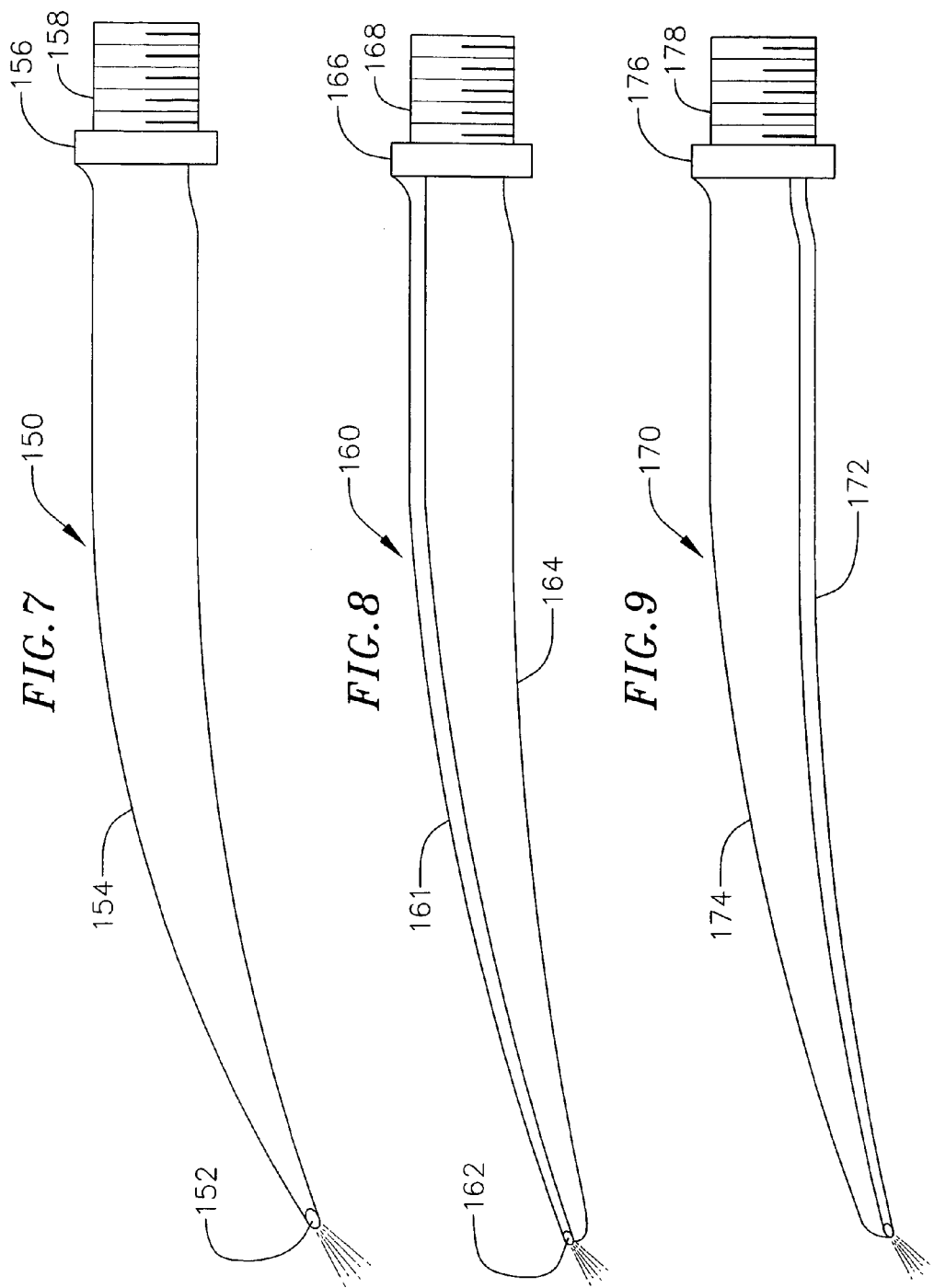

ULTRASONIC DENTAL INSERT HAVING INTERCHANGEABLE PLASTIC AND METAL TIPS

CROSS-REFERENCE TO RELATED APPLICATIONS

This application claims the priority to and the benefit of U.S. Provisional Patent Application No. 60/432,652 entitled "Ultrasonic Dental Tool Insert with Plastic Interchangeable, Disposable Tip" filed Dec. 12, 2002, the entire content of which is incorporated herein by reference.

This application contains subject matter related to the subject matter disclosed in a commonly owned U.S. patent application Ser. No. 10/734,517 now U.S. Pat. No. 7,044,736, entitled "Ultrasonic Dental Insert Having a Hand Grip Fitted to a Retaining Ring," and a commonly owned U.S. patent application Ser. No. 10/735,050, pending, entitled "Ultrasonic Dental Handpiece Having a Rotatable Head," both of which are filed Dec. 12, 2003 and the entire contents of both of which are incorporated herein by reference.

FIELD OF THE INVENTION

The present invention is related to ultrasonic dental tools, and particularly to an ultrasonic dental insert having interchangeable plastic and metal tips.

BACKGROUND

Dental practitioners use ultrasonic dental tools (instruments) for dental treatments and procedures, such as scaling, periodontal treatments, root canal therapy, and the like. The ultrasonic dental tools typically include a handpiece coupled at one end (i.e., a proximal end) to an electrical energy and fluid source via a cable. The cable includes a hose to provide fluid (e.g., water) and conductors to provide electrical energy.

The other end (i.e., a distal end) of the handpiece has an opening intended to receive a replaceable insert with a transducer (e.g., magnetostrictive) carried on the insert. The transducer extends from a proximal end of the insert into a hollow interior of the handpiece. An ultrasonically vibrated tip extends from a distal end of the insert.

The tip of the insert is typically made of a piece of solid metal material which is machined to the desired shape and through which a fluid passage is drilled or otherwise formed for part of the tip length. Such metal tips often produce frictional heat while removing calculus and debris from the tooth and gum surfaces. Also, such metal tip may damage the tooth and/or the gum when applied inside the mouth of a patient. Therefore, it is desirable to provide a non-metal tip. However, as use of metal tips are sometimes desirable, it is desirable to provide an insert having an interchangeable tip, which can be either metal or non-metal depending on the desired application.

SUMMARY

In an exemplary embodiment of the present invention, an ultrasonic dental insert for an ultrasonic dental tool is provided. The ultrasonic dental insert includes a transducer for generating ultrasonic vibrations. A connecting body has a proximal end attached to the transducer and a distal end having an engagement portion formed thereon. A hand grip envelops at least a portion of the connecting body. At least one O-ring is for shock absorption, and is mounted between the connecting body and the hand grip and around the engagement portion. A removable tip engages the engagement portion.

In another exemplary embodiment of the present invention, an ultrasonic dental unit includes an insert, which includes a transducer for generating ultrasonic vibrations. A connecting body has a proximal end attached to the transducer and a distal end having an engagement portion formed thereon. A hand grip envelops at least a portion of the connecting body. At least one O-ring is for shock absorption, and is mounted between the connecting body and the hand grip and around the engagement portion. A removable tip engages the engagement portion. The ultrasonic dental unit also includes an ultrasonic dental handpiece for receiving the insert. The ultrasonic dental handpiece includes a coil assembly for exciting the transducer.

BRIEF DESCRIPTION OF THE DRAWINGS

These and other aspects of the invention may be understood by reference to the following detailed description, taken in conjunction with the accompanying drawings, wherein:

FIG. 1 illustrates an ultrasonic dental unit (or system) including an ultrasonic dental tool attached to an electrical energy & fluid source;

FIG. 2 is a top view of a dental tool insert in an exemplary embodiment of the present invention;

FIG. 3 is a side view of the dental tool insert of FIG. 2, which has been rotated by approximately 90 degrees from the top view depicted in FIG. 2;

FIG. 4 illustrates an interchangeable tip for the dental tool insert of FIG. 2;

FIG. 5 illustrates the interchangeable tip of FIG. 4, which has been rotated by approximately 90 degrees;

FIG. 7 is an interchangeable tip for the dental tool insert in another exemplary embodiment of the present invention;

FIG. 8 is an interchangeable tip for the dental tool insert in yet another exemplary embodiment of the present invention;

FIG. 9 is an interchangeable tip for the dental tool insert in still another exemplary embodiment of the present invention.

DETAILED DESCRIPTION

Figure 6:
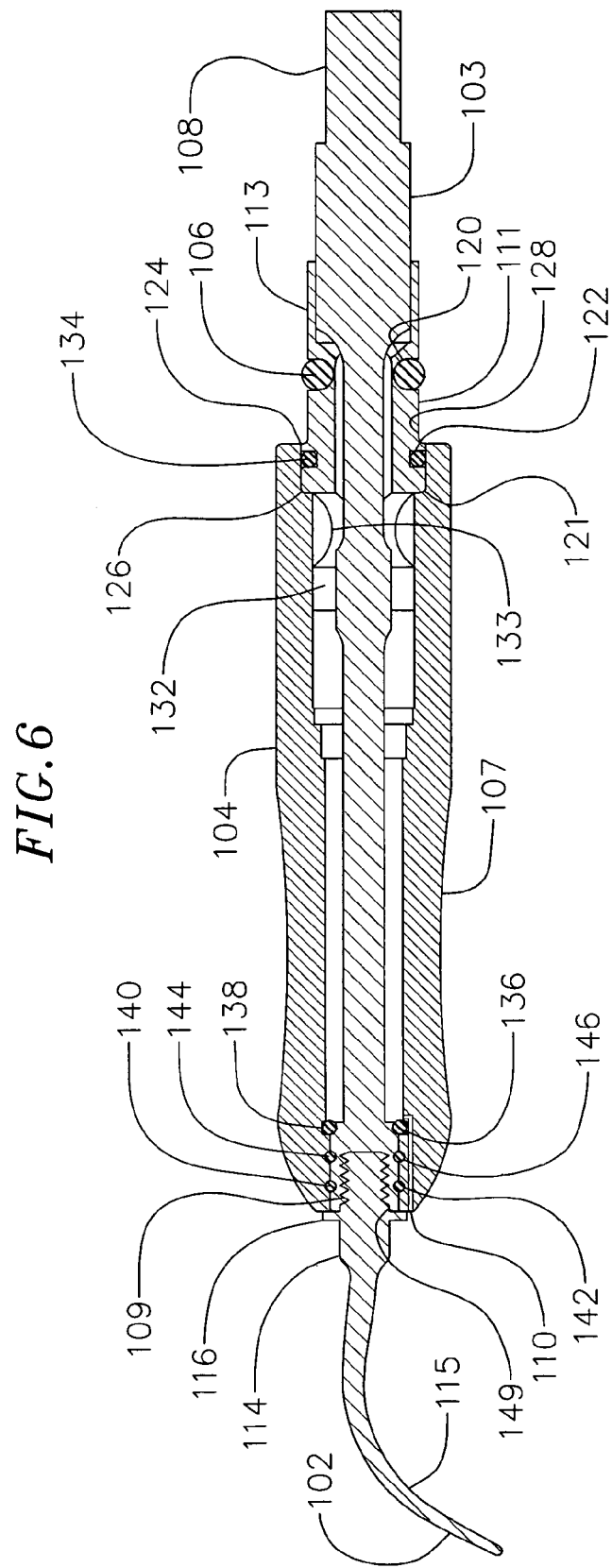
FIG. 6 is a cross-sectional view of the interchangeable tip of FIG. 2, taken along the line A—A.

In exemplary embodiments of the present invention, an ultrasonic dental insert has an interchangeable tip, which can be made of either resin or metal. The connecting body of the insert is configured to have a predetermined relationship with the tip, such that the ultrasonic vibrations generated by the transducer is properly transmitted to the distal end of the tip to be applied on a gum or a tooth of a dental patient.

FIG. 1 illustrates an ultrasonic dental unit including an ultrasonic dental tool 10 attached to an electrical energy & fluid source 14 via a cable 12. The cable 12 includes a conduit for carrying fluid as well as wires for carrying electrical signals from the electrical energy & fluid source 14 to the ultrasonic dental tool 10. The ultrasonic dental tool 10 includes a handpiece 200 and an insert 100 inserted into the handpiece 200.

Referring now to FIGS. 2 and 3, the dental insert 100 includes a tip 102 at its distal end and an ultrasonic transducer 108 at its proximal end. The tip 102 is coupled to the transducer 108 via a connecting body 103, which may take a form of a shaft. The tip is removably attached to the connecting body 103 so that tips can be interchanged depending on the desired application. Further, the tip 102 may be disposed or steam autoclaved after detaching it from the rest of the ultrasonic dental insert. For example, the tip 102 may be made using high temperature plastic such as ULTEM®, which is an amorphous thermoplastic polyetherimide available from GE Plastics, or any other suitable resin plastic. The tip may also be made of metal, such as stainless steel. The term "plastic" is used herein to generally designate synthetic polymeric material such as resin.

The ultrasonic dental insert 100 is designed such that it will work with both metal and plastic tips. Metal tips, for example, may be used for general scaling, cleaning, and the like. Plastic tips may be used to clean sensitive areas as the plastic does not generate the same amount of frictional heat as metal. Therefore, plastic tips may be used around sensitive gum lines, on expensive restorations like crowns and bridges (porcelain) and/or around titanium implants which otherwise may be damaged by a metal tip. Hence, a metal tip may be used for general work, then a plastic tip may be used for delicate work.

The connecting body is made of material suitable for transmitting ultrasonic vibrations such as stainless steel, as it is used to deliver ultrasonic vibrations generated by the transducer 108 to the tip 102. The transducer 108, for example, may be attached to the connecting body 103 by soldering, welding, laser welding and/or any other suitable method. For example, the joint between the connecting body 103 and the transducer 108 may be a braze joint formed using a braze compound, which includes cadmium free silver solder and high temperature brazing flux.

The connecting body 103 has mounted thereon an annular retaining ring 111, which may also be made of metal such as stainless steel. The retaining ring 111 also has a connecting portion 113, which has a generally cylindrical cavity formed therein for receiving a corresponding portion of the connecting body 103 in a force fit relationship. The retaining ring is fixedly attached (e.g., snapped on) to the connecting body 103 such that it neither rotates nor moves laterally along the axis of the connecting body.

The ultrasonic dental insert 100 also includes a hand grip 104, which may be made of high temperature resin. For example, the hand grip 104 may be fabricated using ULTEM® or other suitable resin plastic. The hand grip 104 is a one-piece hand grip, which is mounted on the connecting body 103 and the retaining ring 111 by sliding it over the connecting body 103 and the retaining ring 111. In other embodiments, multi-piece hand grips may be used.

The hand grip 104 has a generally cylindrical shape, and is fitted over the retaining ring 111 and locked in place, such that the retaining ring 111 and the connecting body 103 are secured to the hand grip 104. The hand grip 104 is removably coupled to the connecting body 103 and the retaining ring 111, such that the hand grip can be separated from them.

Along its outer surface, the hand grip 104 has a contour and has a slightly concave area 107, enabling it to be easily grasped by a dental practitioner. The hand grip 104 also has formed thereon a plurality of bumps 105 on its external surface to further facilitate grasping of the device by a dental practitioner. The hand grip 104 has also formed thereon (e.g., defines) a passageway 110 at its distal end near the tip 102 for delivering fluid (e.g., water) to the gum or tooth of the patient.

In other embodiments, the retaining ring for fixing the hand grip may not be used. Instead, the hand grip may be made of two pieces of resin plastic that are fitted together with the connecting body disposed therebetween.

The retaining ring 111 has an opening 112 formed thereon for receiving fluid from the handpiece 200. The fluid may exit through the passageway 110 of the hand grip 104. In other embodiments, the insert 100 may have an opening at the end of its tip 102, a groove formed on the tip, or an external tube for enabling the fluid to exit the insert.

The transducer 108, for example, may be formed from a stack of thin nickel plates (e.g., 16 laminated nickel alloy strips, which are 90% nickel manganese (NiMn)) that are arranged in parallel. The nickel plates may be joined together at both ends at a braze joint using, for example, a braze compound including cadmium free silver solder and high temperature brazing flux. The insert 100 is a magnetostrictive type wherein the nickel plates 108 can convert the electrical energy into ultrasonic vibrations when, for example, coils in the handpiece are energized using the electrical signals from the cable. In other embodiments, the ultrasonic dental insert may use a piezoelectric transducer, as is commonly used in Europe.

The insert 100 has an O-ring 106 mounted thereon for engaging and pressing against the inner surface of the handpiece 200 such as to form a water tight seal. For handpieces having a rotatable rotator head, the O-ring 106 may engage the rotator head such that the ultrasonic dental insert rotates together with the rotator head.

During operation, the stack of thin nickel plates 108 vibrates at a frequency equal to the stack's natural frequency with excitation induced by coils. After placing the insert in the handpiece and the electrical energy source is powered on, the operator manually tunes the frequency of the electrical energy source until it reaches the resonance frequency, i.e., the natural frequency of the insert. Alternatively, autotune units may automatically lock on the insert resonance frequency once powered on. At this time, the stack begins vibrating. This vibration of the stack is amplified and transmitted to the tip 102 through the connecting body 103. Ultrasonic inserts used in the United States are typically designed to vibrate at 25 kHz or 30 kHz frequencies.

In one exemplary embodiment, the ultrasonic dental insert 102 has the following dimensions. The hand grip has a length of approximately 4.76 centimeter (cm), and an external diameter that ranges from approximately 0.95 cm to 1.11 cm. Further, the retaining ring has a length of approximately 2.22 cm, and a diameter of approximately 0.64 cm. The length of the transducer 108 is approximately 9.65 cm. In addition, the thickness of the stack of nickel plates 108 is approximately 0.48 cm. Further, the length of the connecting body 103 (except for the tip) is approximately 6.74 cm. For the tip, the length of a projection of the tapered portion 115 on a plane is approximately 1.89 cm. In addition, the diameter of the narrowest end of the tip is approximately 0.06 cm, whereas the diameter of the broadest end of the tip is approximately 0.16 cm. Of course, ultrasonic dental inserts in other embodiments may have various different dimensions as those skilled in the art would appreciate.

Referring now to FIGS. 4 and 5, the tip has an elongated tapered portion 115, and a cylindrical interface portion 114. It can be seen in FIG. 5 that the tapered portion 115 is curved. The tapered portion 115 has a circular cross section whose diameter decreases gradually from the end abutting the interface portion 114 ("the proximal end") to the other end of the tip ("the distal end"). The distal end is applied to the gum/teeth of the patient during the dental procedures.

When the tip 102 is made of high temperature plastic (or resin), it reduces frictional heat associated with removing calculus and debris from the tooth and gum surfaces. Also, plastic tips reduce the chance of inflicting damage to the tooth and/or the gum when applied within the patient's mouth. The tip 102 may also be made of metal such as stainless steel, and such metal and plastic tips are interchangeable, and work effectively to apply ultrasonic vibrations to the tooth and/or gum.

The tip 102 has attached to the interface portion 114 a threaded portion 109 and a flange 116. The thread on the threaded portion 109 is formed such that it will engage a threaded opening formed on the handle. Using the thread 109, the tip 102 is made removable. Such removability allows the tip 102 to be a disposable tip that is replaced after a single patient use. In other embodiments, the removable tips may also be pressure fit into a corresponding opening on the connecting body 103.

Since the tip 102 has a very small diameter, it is subject to breakage if too much ultrasonic vibrations are applied to it. On the other hand, if insufficient vibrations are applied, the ultrasonic dental tool 10 (of FIG. 1) may not work effectively. Therefore, the connecting body 103 and the tip 102 should be designed such that a proper level of vibrations are applied to the tip. Since a plastic tip is more likely to break than the metal tip, a shock absorbing mechanism is used on the connecting body 103 to reduce the shock to the plastic tip.

Referring now to FIG. 6, the shock absorbing mechanism is described. The connecting body 103 has formed thereon a threaded tap 149 for screwing in the tip 102. The word "tap" will refer hereinafter to a threaded opening formed at the distal end of the connecting body 103 for engaging the threaded portion 109. The threaded portion 109 engages a corresponding thread on the inner surface of the threaded tap 149 such that the tip 102 is received by the connecting body 103.

The connecting body 103 has formed surrounding the threaded tap 149 a pair of grooves 142 and 146 for seating O-rings 140 and 144, respectively. The O-rings absorb shock such that the vibrations "felt" by the tip are reduced (i.e., dampened), thereby reducing the chance of breaking the plastic tip. In other embodiments, the connecting body may have only one or more than two O-rings mounted thereon for such shock absorption purposes. In still other embodiments, the threaded portion 109 may have a diameter that is substantially smaller than the diameter of the interface portion 114 such that the threaded tap portion has substantially the same diameter as the rest of the connecting body 103.

The connecting body 103 has also formed thereon a circular groove 138 near its distal end. An O-ring 136 is seated in the groove 138. When the hand grip 104 is fitted onto the connecting member 103, the O-ring 136 provides a seal between the connecting member 103 and the hand grip 104 so as to prevent undesired fluid leakage.

The retaining ring 111 has a generally cylindrical shape, and has formed thereon a connecting portion 113 fitting over a corresponding cylindrical portion of the connecting body 103. The opening 112 for receiving fluid from the handpiece is formed on the side of the connecting portion 113. The retaining ring 111 has formed thereon, adjacent to the connecting portion 113, a circular groove 120 for seating the external O-ring 106.

At the distal end, the retaining ring 111 has formed thereon a pair of gripping elements 132 that face each other. Each gripping element has an end portion that protrudes inwardly toward the end portion of the other gripping element. The connecting body 103 has a pair of indentations 130 formed thereon for receiving the protruding end portions of the gripping elements such that the gripping elements 132 are snapped into the indentations 130. Thus engaged, the retaining ring 111 of the illustrated embodiment is locked to the connecting body 103, and neither rotates nor moves laterally with respect to the same.

The hand grip 104 on its inner surface may have formed thereon an inward protrusion 133 for guiding the hand grip 104 to fit over the retaining ring 111. The protrusion 133, for example, engages a gap between the gripping elements 132 so that the hand grip 104 is not rotatable with respect to the connecting body 103, once the hand grip 104 is fitted over the connecting body 103.

The retaining ring 111 also has formed thereon circular flanges 121, 124 and a circular groove 122. The circular groove 122 is for seating an O-ring 134. The hand grip 104 has an undercut 126 formed therein for fitting over the distal end of the retaining ring 111, and engaging the flange 121. The undercut, for example, is circular in shape.

The hand grip 104 has also formed thereon a depressed region 128 below the undercut on its inner surface, which is used to engage the flange 124 and further prevent the retaining ring 111 from moving into the hand grip 104. The depressed region 128, for example, is also circular in shape, wherein the depressed region 128 has a radius larger than that of the undercut 126. The undercut 126 and the depressed region 128 fit tightly with the flanges 121 and 124, respectively.

Referring now to FIGS. 7–9, the tips 150, 160 and 170 are used for an ultrasonic dental insert, and may replace the tip 102. The removable tips of FIGS. 7–9 are slightly curved, and each have a substantially circular cross section. The diameter of the circular cross-section gradually decreases from the proximal end to the distal end. The removable tips, for example, may be made of high temperature plastic such as ULTEM®. The removable tips may be disposable, and have respective threads formed thereon for mounting to the handle of the dental tool insert. The removable tips may also be made of metal such as stainless steel and/or other suitable materials. The removable tips illustrated in FIGS. 5 and 7–9 may be interchanged during ultrasonic dental procedures.

Referring now to FIG. 7, the removable tip 150 has a tapered portion 154 having an opening 152 at a distal end and a flange 156 at a proximal end. The removable tip 150 has a threaded portion 158 attached to the flange 156 for attaching the tip to the connecting body. The tapered portion has formed through its length a conduit or a channel for carrying/delivering fluid from the proximal end (closer to the connecting body) to the distal end. Such fluid (e.g., water) may be applied under pressure as a stream and used for cutting, cooling and/or treatment purposes. Such fluid may also be used to clean the area in the mouth of the patient on whom the dental procedure has been performed. Such fluid may exit the tip through the opening 152.

Referring now to FIG. 8, the removable tip 160 has a tapered portion 164 attached to a flange 166, which in turn is attached to a threaded portion 168 for attaching the tip to a connecting body. The removable tip 160 has attached along the length of its external surface an external tube 161 for carrying fluid. The external tube 161 has an opening 162 at its distal end for applying the fluid (e.g. water) to the patient's mouth. Such fluid can be used for cutting, cooling, treatment and/or cleaning purposes.

Referring now to FIG. 9, the removable tip 170 has a tapered portion 174 attached to a flange 176, which in turn is attached to a threaded portion 178 for attaching the tip to a connecting body. The tapered portion 174 has formed along the length of its external surface an external groove 172 for carrying fluid. The external groove 172 can be used to apply the fluid (e.g., water) to the patient's mouth. Such fluid can be used for cutting, cooling, treatment and/or cleaning purposes.

Figure 10:
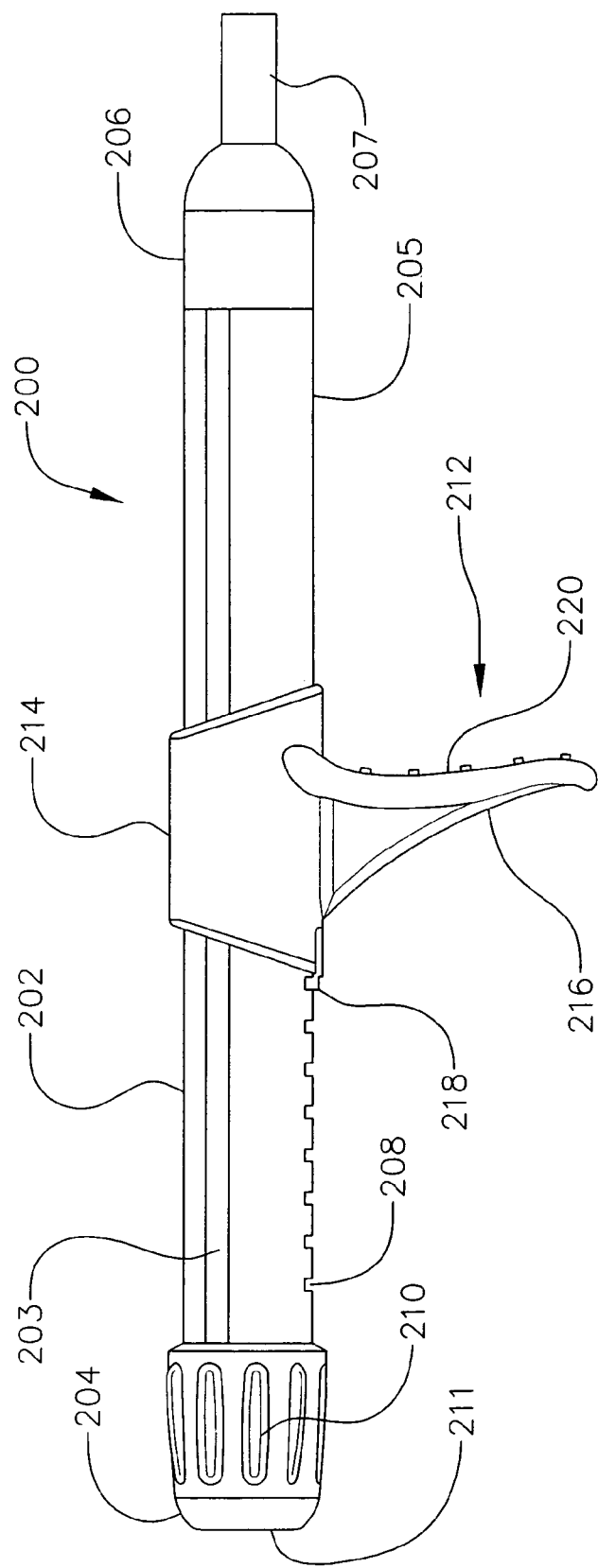
FIG. 10 is a side view of an ultrasonic dental handpiece that can be used with the ultrasonic dental insert of FIG. 2.

FIG. 10 illustrates a side view of a handpiece 200 that can receive the insert 100 as seen, for example, in FIG. 1. The handpiece 200 includes a body 202, a rotator head 204 and an interconnect 206. The rotator head 204 located at a distal end of the handpiece 200 is rotatably coupled to the rest of the handpiece 200. When the insert 100 is installed in the handpiece 200, the O-ring 106 is pressure fitted with an inner surface of the rotator head 204, such that the insert 100 rotates together with the rotator head 204.

The interconnect 206 located at a proximal end of the handpiece 200 is coupled to a cable (e.g., the cable 12 of FIG. 1) for providing electrical signals as well as fluid (e.g., water) to the handpiece 200. The interconnect 206 has a strain reliever 207 formed thereon to relieve strain between the interconnect 206 and the cable.

Since the body 202 is fixedly coupled to the interconnect 206, which in turn is fixedly attached to the cable, the handpiece 200 cannot be rotated easily. Therefore, by allowing the rotator head 204 to rotate with respect to the rest of the handpiece 200, the dental practitioner need not repeatedly re-orient the entire dental tool to treat different teeth and/or different areas of a tooth. Further, since the rotator head 204 of the handpiece 200 can be rotated rather easily with respect to the body 202, the dental practitioner need not take the insert out of the patient's mouth and rotate the insert using both hands to re-orient the tip of the insert at a desired angular position. Therefore, time associated with re-orienting the tip a number of times during the dental treatment is reduced, and the flow of work is not interrupted as much, thereby resulting in a smooth work flow and reduction of time.

The rotator head 204 has a generally cylindrical shape, a hollow interior, and an opening at each end of the interior, which is used to receive the distal end of the body 202 at one end and a dental insert at the other end. For example, at its distal end, the rotator head 204 has formed thereon an opening 211 for receiving the ultrasonic dental insert 100.

The rotator head 204 has formed around its outer peripheral surface a plurality of indentations 210. Each indentation 210 has an elongated elliptical (or rectangular) shape with its major axis in the direction parallel to the central axis of the handpiece 200. The indentations 210 facilitate grasping of the rotator head 204 by a dental practitioner to rotate, for example, it with respect to the body 202 (e.g., using only one hand). In other embodiments, the rotator head 204 may have a number of protrusions formed thereon instead of the indentations.

The body 202 has formed thereon a pair of grooves 203 that are equidistant from the top and traverse substantially the whole length of the body 202. The grooves 203 are used to mount a hand grip 212 on the handpiece 200. The body 202 has also formed thereon at its bottom near the distal end of the body 202 a plurality of substantially evenly spaced slots 208 that are used to keep the hand grip 212 from moving in the direction of the axis of the handpiece 200. The body 202 has also formed thereon at its bottom near the proximal end a groove 205 that is co-linear to the slots 208. The groove 205 engages the hand grip 212 together with the grooves 203 to keep the hand grip 212 from rotating about the central axis of the handpiece 200. The grooves may not be used in other embodiments.

The hand grip 212 has an engagement portion 214, which has a generally cylindrical shape and a hollow interior. The engagement portion 214 is slipped onto the body 202 similar to a sleeve, and engages the body 202 such that the engagement portion envelopes a portion of the body 202. The engagement portion has formed thereon a resilient cantilever portion 218, which is used to engage one of the slots 208 on the body 202. The engagement portion 214 has attached to its bottom surface a handle 216, which is used by a dental practitioner to hold the handpiece 200 during dental procedures. The handle also facilitates rotating of the rotator head 204 using one hand. The handle 216 has formed on its back surface a plurality of indentations or protrusions 220, which are used to facilitate grasping by a dental practitioner.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

We claim:

1. An ultrasonic dental insert for an ultrasonic dental tool, comprising:
   a transducer for generating ultrasonic vibrations;
   a connecting body having a proximal end and a distal end, the proximal end attached to the transducer, the distal end having an engagement portion formed thereon;
   a hand grip enveloping at least a portion of the connecting body;
   at least one o-ring mounted between the connecting body and the hand grip to provide a seal between the connecting body and the hand grip;
   a removable tip adapted to engage the engagement portion, wherein the removable tip is made of plastic; and
   at least one O-ring for shock absorption, mounted on the connecting body and around the engagement portion in the vicinity of a location where the tip engages the engagement portion.

2. The ultrasonic dental insert of claim 1, further comprising at least one other removable tip made of resin or metal, wherein the at least one other removable tip is interchangeable with the removable tip.

3. The ultrasonic dental insert of claim 1, wherein the removable tip comprises an attachment portion for engaging the engagement portion.

4. The ultrasonic dental insert of claim 3, wherein the removable tip comprises a tapered portion coupled to the attachment portion.

5. The ultrasonic dental insert of claim 4, wherein the tapered portion has a generally conical wall that defines a conduit therethrough for carrying fluid used during ultrasonic dental procedures.

6. The ultrasonic dental insert of claim 4, wherein the removable tip further comprises an external tube attached along the tapered portion for carrying fluid used during ultrasonic dental procedures.

7. The ultrasonic dental insert of claim 4, wherein the tapered portion has a groove formed thereon for carrying fluid used during ultrasonic dental procedures.

8. The ultrasonic dental insert of claim 4, wherein the tapered portion has a substantially circular cross section whose diameter decreases gradually from a first end near the connecting body to a second end.

9. The ultrasonic dental insert of claim 4, wherein the tapered portion includes a first portion which is generally aligned with the connecting body, and a second portion which is curved at an angle from the first portion.

10. The ultrasonic dental insert of claim 3, wherein the attachment portion is threaded to engage the engagement portion, which is also threaded.

11. The ultrasonic dental insert of claim 10, wherein the engagement portion comprises a generally cylindrical wall defining a threaded tap for receiving the attachment portion.

12. The ultrasonic dental insert of claim 3, wherein the engagement portion comprises a generally cylindrical wall defining a cavity, and the attachment portion is pressure fit into the cavity.

13. The ultrasonic dental insert of claim 1, wherein the hand grip has formed thereon a plurality of bumps for facilitating grasping by a dental practitioner.

14. An ultrasonic dental unit comprising:
an insert comprising:
- a transducer for generating ultrasonic vibrations;
- a connecting body having a proximal end and a distal end, the proximal end attached to the transducer, the distal end having an engagement portion formed thereon;
- a hand grip enveloping at least a portion of the connecting body;
- at least one o-ring mounted between the connecting body and the hand grip to provide a seal between the connecting body and the hand grip;
- a removable tip adapted to engage the engagement portion, wherein the removable tip is made of plastic;
- at least one O-ring for shock absorption, mounted on the connecting body around the engagement portion in the vicinity of a location where the tip engages the engagement portion; and
an ultrasonic dental handpiece for receiving the insert and comprising a coil assembly for exciting the transducer.

15. The ultrasonic dental unit of claim 14, further comprising at least one other removable tip made of metal or resin, wherein the at least one other removable tip is interchangeable with the removable tip.

16. The ultrasonic dental unit of claim 14, further comprising an electrical energy and fluid source for providing electrical signals for energizing coil assembly and fluid to the ultrasonic dental handpiece.

17. The ultrasonic dental unit of claim 14, wherein the removable tip comprises an attachment portion for engaging the engagement portion.

18. The ultrasonic dental insert of claim 17, wherein the attachment portion is threaded to engage the engagement portion, which is also threaded.

19. The ultrasonic dental insert of claim 18, wherein the engagement portion comprises a generally cylindrical wall defining a threaded tap for receiving the attachment portion.

20. The ultrasonic dental insert of claim 17, wherein the engagement portion comprises a generally cylindrical wall defining a cavity, and the attachment portion is pressure fit into the cavity.

21. The ultrasonic dental unit of claim 17, wherein the removable tip comprises a tapered portion coupled to the attachment portion.

22. The ultrasonic dental unit of claim 21, wherein the tapered portion has a generally conical wall that defines a conduit therethrough for carrying fluid used during ultrasonic dental procedures.

23. The ultrasonic dental unit of claim 21, wherein the removable tip further comprises an external tube attached along the tapered portion for carrying fluid used during ultrasonic dental procedures.

24. The ultrasonic dental insert of claim 21, wherein the tapered portion has a groove formed thereon for carrying fluid used during ultrasonic dental procedures.

25. The ultrasonic dental insert of claim 21, wherein the tapered portion has a substantially circular cross section whose diameter decreases gradually from a first end near the connecting body to a second end.

* * * * *